United States Patent [19]

Kudsk

[11] Patent Number: 5,646,005

[45] Date of Patent: Jul. 8, 1997

[54] USE OF AN IL-6 ASSAY FOR PREDICTING THE DEVELOPMENT OF POST-TRAUMA COMPLICATIONS

[76] Inventor: Kenneth A. Kudsk, 956 Court Ave., Memphis, Tenn. 38163

[21] Appl. No.: 234,154

[22] Filed: Apr. 28, 1994

[51] Int. Cl.$^6$ .................................................. G01N 33/543
[52] U.S. Cl. ...................... 435/7.32; 435/7.24; 435/7.92; 436/86; 436/518
[58] Field of Search ............................ 424/158.1, 195.11, 424/198.1; 530/351, 388.3, 388.73, 389.7; 422/68.1; 435/7.29, 7.32, 7.92; 436/518, 86

[56] References Cited

PUBLICATIONS

Corcoron et al., An Enzyme Immunoassay for the Quantitation of Human Interleuken 6 Clin. Chem. 37(6), 1046, (1991).

Helfgott et al., Multiple Forms of IFNB$_2$/IL–6 in Sreum and Body Fluids during Acute Bacterial Infection J. Immunol. 142(3), 948–953, (1989).

Brozik et al., Interleukin 6 Levels in Synovial Fluids of Patients with Different Arthritises J. Rheumatology 19, 63–68 (1992).

van Oers et al., Interleukin 6 (IL–6) in Serum and Urine of Renal Transplant Recipients Clin. Exp. Immunol. 71: 314–319 (1988).

Eisenberg, R.L., TRIIS Methodology in Penetrating Trauma: 198 Patients at Baragwanath Hospital Aust. N.Z. J. Surg. 63, 515–519 (1993).

Suoboda et al., Dynamics of Interleukin 1, 2, and 6 and Tumor Necrosis Factor Alpha in Multiple Trauma Patients J. Trauma 36(3), 336–340 (1994).

Heck et al., Increased Plasma Levels of Interleukin–6 in Sepsis Blood 74(5), 1704–1710, (1989).

Drost et al., Plasma Cytokiner Following Thermal Injury and Their Relationship with Patient Mortality, Burn Size, and Time Postburn. J. Trauma 35(3), 335–339, (1993).

Baigrie et al., Systemic Cytokine Response after Major Surgery Br. J. Surg. 79, 757–760 (1992).

Brailly et al., Total Interleukin 6 in Plasma Measured by Immunoassay Clin. Chem. 40(1), 116–123, (1994).

*Primary Examiner*—David Saunders
*Attorney, Agent, or Firm*—Howrey & Simon; Richard Kjeldgaard; Jeffrey I. Auerbach

[57] ABSTRACT

Diagnostic methods are described for using the concentration of a cytokine present in serum or other biological fluids in rder to predict the predisposition of an individual to post-trauma infectious and or inflammatory complications. Also described are diagnostic kits that are particularly suitable for use in such diagnosis.

16 Claims, No Drawings

USE OF AN IL-6 ASSAY FOR PREDICTING THE DEVELOPMENT OF POST-TRAUMA COMPLICATIONS

FIELD OF THE INVENTION

The present invention is in the field of diagnostics, and more specifically relates to the use of an assay for a cytokine (such as interleukin-6) as a means for predicting the occurrence of infectious complications in a patient recovering from surgery or trauma. The invention also relates to diagnostic kits that are particularly suitable for use in such diagnosis.

BACKGROUND OF THE INVENTION

I. Cytokines and the Acute Phase Response

Infection, injury, trauma, and a variety of other immunological disorders provoke a basic immune system defense response known as the "acute phase response." (Van Snick, J., *Annu. Rev. Immunol.* 8:253–278 (1990); Akira, S. et al., *Immunol. Rev.* 127:25–50 (1992); Koj, A. In: *The Acute Phase Response to Injury and Infection*, Elsevier, Amsterdam, vol. 10, p139 (1985)). The acute phase response is part of the general inflammatory host defense mechanism. The acute phase response is characterized by fever, leukocytosis, negative nitrogen balance, increased vascular permeability, alterations in plasma meta and steroid concentrations, and by an increase in the synthesis of hepatic acute phase proteins (such as $\alpha_1$-antitrypsin, $\alpha_1$-antichymotrypsin, and other protease inhibitors, serum amyloid A, and C-reactive proteins) (Van Snick, J., *Annu. Rev. Immunol.* 8:253–278 (1990)).

Various proteins (termed "cytokines") are involved in mediating the acute phase response. These cytokines include tumor necrosis factor ("TNF"), transforming growth factor-$\beta$ ("TGF-$\beta$"), Interleukin-1 ("IL-1"), Interleukin-2 ("IL-2"), Interleukin-8 ("IL-8"), Interleukin-10 ("IL-10") and Interleukin-6 ("IL-6") (Bauer, J. et al., *Ann. Hematol.* 62:203–210 (1991); Kishimoto, T., *Blood* 74:1–10 (1989); Akira, S. et al., *Immunol. Rev.* 127:25–50 (1992); Van Snick, J., *Annu. Rev. Immunol.* 8:253–278 (1990)).

IL-6 plays a central role in inducing the acute phase response. Its release produces multiple effects. IL-6 induces B cells to synthesize immunoglobulins; it induces fever, promotes the synthesis of corticotropin by the pituitary, stimulates hepatocyte production of the acute phase proteins, and acts as a growth promoter of mesangial cells and keratinocytes. IL-6 exerts its control on acute phase proteins at least in part at the transcriptional level (Morrone, G. et al., *J. Biol. Chem* 263:12554–12558 (1988)). IL-6 also is believed to play a role in inducing the proliferation of hematopoietic cells, and particularly, cytotoxic T cells.

IL-6 is produced by a large number of cell types, including fibroblasts, endothelial cells, keratinocytes, monocytes-macrophages, T-cells, mast cells, and a variety of tumor cell lines (Van Snick, J., *Annu. Rev. Immunol.* 8:253–278 (1990); Bauer, J. et al., *Ann. Hematol.* 62:203–210 (1991)). Accessory cells appear to produce the major source of IL-6, however, significant amounts of IL-6 are also produced by lymphocytes (Hirano, T. et al., *Eur. J. Immunol.* 18:1797–1801 (1988)).

IL-6 is a protein of 21–28 kD which exhibits extensive post-translational modification. cDNA encoding IL-6 has been cloned, and predicts a precursor protein of 212 amino acids including a hydrophobic signal sequence of 28 residues (Hirano, T. et al., *Nature* 324:73–76 (1986)). Recombinant human IL-6 can be obtained from Genzyme Corp., Boston, Mass.

IL-6 is secreted into the serum. Normal serum levels of IL-6 are less than 5 pg/ml (Nachbaur, D. M. et al, *Ann. Hematol.* 62:54–58 (1991)). The protein is not generally produced constitutively by normal cells (Akira, S. et al., *Immunol. Rev.* 127:25–50 (1992)). Indeed, constitutive expression is a characteristic of a number of pathologic conditions (such as psoriasis, rheumatoid arthritis, cardiac myxoma, multiple myeloma, Castleman's disease, and HIV infection. The level of IL-6 is regulated by positive or negative stimuli. For example, liposaccharides induce cells to produce IL-6; the secretion of glucocorticoids represses IL-6 expression (Akira, S. et al., *Immunol. Rev.* 127:25–50 (1992)). Other positive inducers of IL-6 production include viruses, interleukin-1 (IL-1), interleukin-3 (IL-3), granulocyte/macrophage-colony stimulating factor (GM-CSF), tumor necrosis factor (TNF), $\beta$-interferon, and platelet-derived growth factor. IL-6 production is induced during acute inflammatory processes, and is produced by cells that have been injured.

IL-6 induction rapidly follows injury or trauma. Plasma levels of IL-6 can be detected as early as 30 minutes after incision in patient's undergoing elective surgery (Shenkin, A. et al., *Lymphok. Res.* 8:123–127 (1989)). Maximal levels of IL-6 are found between 90 minutes and 6 hours post surgery (Pullicino, E. A. et al., *Lymphok. Res.* 9:2–6 (1990); Shenkin, A. et al., *Lymphok. Res.* 8:123–127 (1989)). In contrast, upon exposure to an infectious agent, elevated plasma levels may persist for days (Bauer, J. et al., *Ann. Hematol.* 62:203–210 (1991)). Maximal IL-6 plasma concentrations after sterile trauma, such as elective surgery, are about 100 pg/ml, which is orders of magnitude less than the level (up to 500 ng/ml) associated with bacterial infection (Fiedler, W. et al., *Leukemia* 4:462–465 (1990); Helfgott, D. C. et al., *J. Immunol.* 142:948–953 (1989)). Elevated serum levels of IL-6 have been observed in transplant rejection, and inflammatory bowel disease (van Oers, M. H. J. et al., *Clin. Exper. Immunol.* 71:314–319 (1988); Bauer, J. et al., *Ann. Hematol.* 62:203–210 (1991)).

II. Assays for Interleukin-6

A. Biological Assays

The observation that a pulse of increased IL-6 synthesis can be observed in the normal response to many kinds of traumatic or infectious events has led to the development of assays for detecting and quantifying serum or urine IL-6 levels.

Since IL-6 has a hybridoma growth promotant activity, the capacity of a patient's serum to support hybridoma growth provides a biological assay for IL-6. Other biological assays exploit the capacity of IL-6 to stimulate the growth of B-cells (Hirano, T. et al., *Proc. Natl. Acad. Sci. (U.S.A.)* 82:5490–5494 (1985); Yoshizaki, K. et al., *Blood* 74:1360–1367 (1989)). Indeed, certain B-cell lines require IL-6 as an essential growth factor, and have been used to define sensitive bioassays of IL-6 concentration (Akira, S. et al., *FASEB J.* 4:2860–2867 (1990); Lansdorp, P. M. et al., *Curr. Top. Microbiol. Immun.* 132:105–113 (1986); Matsuda, T. et al., *Eur. J. Immunol.* 18:951–956 (1988); Nijsten, M. W. N. et al., *Lancet* 2:921 (1987); Van Snick, J. et al., *Proc. Natl. Acad. Sci. (U.S.A.)* 83:9679–9684 (1986); Nachbaur, D. M. et al., *Ann. Hematol.* 62:54–58 (1991); Ershler, W. B. et al., *Lymphok. Cytok. Res.* 12:225–230 (1993)).

Sensitivity for assays of IL-6 in the range of 20–100 pg/ml have been reported (Brozik, M. et al., *J. Rheumatol.*

19:63–68 (1992)). The bioassays require significant incubation times (e.g., 4 days) in order to provide a final result (Nachbaur, D. M. et al., *Ann. Hematol.* 62:54–58 (1991); Brozik, M. et al., *J. Rheumatol.* 19:63–68 (1992)).

B. Immunoassays

The availability of antibodies that are capable of specifically binding IL-6 has permitted the development of sensitive immunoassays of IL-6 concentration. Such antibodies can be obtained from Genzyme Corp. (Boston, Mass.), or from R&D Systems, Inc. (Minneapolis, Minn.).

Immunoassays are assay systems that exploit the ability of an antibody to specifically recognize and bind to a particular target molecule. Immunoassays are used extensively in modern diagnostics (Fackrell, *J. Clin. Immunoassay* 8:213–219 (1985)). A large number of different immunoassay formats have been described (Yolken, R. H., *Rev. Infect. Dis.* 4:35 (1982); Collins, W. P., In: *Alternative Immunoassays*, John Wiley & Sons, NY (1985); Ngo, T. T. et al., In: *Enzyme Mediated Immunoassay*, Plenum Press, NY (1985)).

Corcoran, K. A. et al. (*Clin. Chem.* 37:1046 (1991)) discuss an enzyme immunoassay for the quantification of IL-6 in serum. The assay is stated to be capable of detecting 2.6 pg/ml. A double antibody enzyme-linked immunoassay for IL-6 has been used to determine IL-6 concentrations in synovial fluids (Brozik, M. et al., *J. Rheumatol.* 19:63–68 (1992)). The assay required only a 1 hour incubation period, however, its sensitivity was 80-fold lower than that of bioassays (i.e. the level of detection was 80 pg/ml). As stated, normal serum levels of IL-6 are less than 5 pg/ml (Nachbaur, D. M. et al., *Ann. Hematol.* 62:54–58 (1991)). Thus, the double antibody enzyme-linked immunoassay could not be used to evaluate IL-6 serum levels (Brozik, M. et al., *J. Rheumatol.* 19:63–68 (1992)).

Alternate IL-6 immunoassay protocols have been described by Buyalos, R. P. et al. (*Fertil. Steril.* 57:1230–1234 (1992)), and by Thavasu, P. W. et al. (*J. Immunol. Meth.* 153:115–124 (1992)). The assay of Buyalos, R. P. et al. was used to measure IL-6 levels in follicular fluids. The assay's detection limit was 50 pg/ml. The assay of Thavasu, P. W. et al. was used to assay IL-6 in blood, and had a detection level of 70 pg/ml. The assay exhibited problems of stability and irreproducibility (Thavasu, P. W. et al, *J. Immunol. Meth.* 153:115–124 (1992)).

A commercially available immunoassay tests for IL-6 (IL-6 EASIA, Medgenix Diagnostics) has been described (Söderquist, B. et al., *Scand. J. Immunol.* 24:607–612 (1992)). The test is based upon an oligoclonal capture antigen system in which several monoclonal antibodies directed against distinct epitopes of IL-6 are used. A solid phase monoclonal immunoassay for IL-6 has also been described (Helle, M. et al., *J. Immunol. Meth.* 138:47–56 (1991)).

Elevated IL-6 plasma levels have been found in patients in sepsis (Hack, C. E. et al., *Blood* 74:1704–1710 (1989); Waage, A. et al., *J. Exper. Med.* 169:333–338 (1989)). However, efforts to correlate the kinetics of IL-6 levels with the severity of septicemia have not yielded clear results. One study, involving *S. aureus*-induced indicated that the diagnostic value of IL-6 analyses depended upon the availability of other information, such as the C-reactive protein levels in a patient (Söderquist, B. et al., *Scand. J. Immunol.* 24:607–612 (1992)). A second study of the relationship between IL-6 kinetics and septicemia noted high levels of IL-6 were found in patients experiencing septic shock, but not in patients experiencing both septic shock and meningitis (Waage, A. et al., *J. Exper. Med.* 169:333–338 (1989)). Even in patients experiencing septic shock, a 1,000–10,000 fold range of IL-6 levels was encountered (Waage, A. et al., *J. Exper. Med.* 169:333–338 (1989)). A third study of the relationship between IL-6 kinetics and septicemia noted that higher levels of IL-6 were seen in those patients who died from sepsis relative to those who survived, however, no correlation was observed between survival time and IL-6 plasma level (Hack, C. E. et al., *Blood* 74:1704–1710 (1989)). Indeed, IL-6 levels became undetectable in one patient who ultimately succumbed to sepsis (Hack, C. E. et al., *Blood* 74:1704–1710 (1989)).

As indicated, IL-6 levels rise after elective surgery. The extent of the rise can be correlated to the duration or severity of the surgery (Cruikshank, A. M. et al., *Clin. Sci.* 79:161–165 (1990)). IL-6 levels for all types of surgery evaluated fell to baseline levels within 4–5 days (Cruikshank, A. M. et al., *Clin. Sci.* 79:161–165 (1990)). Investigations of the relationship between the change in IL-6 levels and post-surgical trauma have also been conducted. No correlation was found between IL-6 levels and hematopoietic recovery of patients who had received peripheral blood stem cell autographs (Kawano, Y. et al., *Blood* 81:856–860 (1993)).

Thus, despite the significance of IL-6 in acute inflammatory diseases, and the existing methods for assaying IL-6, such assays have been considered to be of limited diagnostic value (Bauer, J. et al., *Ann. Hematol.* 62:203–210 (1991)). In particular, IL-6 levels are elevated for only a short period of time, and IL-6 synthesis may be associated with a large number of disease states. Thus, the art indicates that both the absence and the presence of IL-6 levels in serum may be unrelated to a particular injury or trauma (Bauer, J. et al., *Ann. Hematol.* 62:203–210 (1991)).

As will be appreciated, the capacity to diagnose septicemia or other inflammatory process prior to the onset of life threatening clinical manifestations would be highly desirable. Previous efforts to correlate IL-6 levels with such complications have suggested that changes in IL-6 levels are too transient, and too variable to permit a definitive correlation. A method for using IL-6 levels in serum or other biological fluids in order to diagnose the predisposition of an individual to post-trauma complications would, however, be highly desirable. The present invention provides such a method.

SUMMARY OF THE INVENTION

Thus, the present invention concerns the use of cytokine levels in biological fluids to diagnose the predisposition of an individual to a post-trauma complication. The invention is additionally directed to diagnostic kits suitable for use in this method.

In detail, the invention provides a method for determining the predisposition of an individual to a complication of trauma prior to the onset of overt clinical symptoms of such complication, which comprises determining the concentration of a cytokine (especially interleukin-6) present in a biological fluid of the individual about one day post-trauma.

The invention particularly pertains to the embodiments wherein the trauma is a blunt trauma (such as a poisoning, a fall, a simple fracture, a crush or a burn) or wherein the trauma is a penetrating trauma (such as a wound, a complex fracture, or a surgical procedure).

The invention particularly pertains to the embodiments wherein the complication comprises an infection (especially septicemia, bacteremia, pneumonia, an intra-abdominal abscess, empyema.

The invention is particularly directed to the use of an immunoassay to determine cytokine concentration.

The invention is also directed to the embodiment of the above methods which further entails determining the age of the patient, the mechanism of injury, the nature of feeding, or the Abdominal Trauma Index, or the Injury Severity Score associated with the trauma of the individual.

DETAILED DESCRIPTION OF THE INVENTION

I. The Correlation Between Cytokine Concentration And Post-Trauma Complications The present invention derives, in part, from the recognition of the existence of a correlation between the post-trauma level of a cytokine in a biological fluid of a patient who has experienced trauma and the predisposition of that patient to subsequent post-surgical or post-trauma complications, especially infection. The capacity to identify such a predisposition permits one to predict whether a particular patient will experience infection, prior to the actual recognition of overt clinical symptoms of such infection. The ability to predict post-trauma infection permits earlier and more effective therapeutic intervention, and lowers the overall costs and complexity associated with post-trauma patient management.

The cytokines of interest to the present invention include those whose levels correlate with a predisposition to infection. Such cytokines include tumor necrosis factor ("TNF"), transforming growth factor-β ("TGF-β"), Interleukin-1 ("IL-1"), Interleukin-2 ("IL-2"), Interleukin-8 ("IL-8"), Interleukin-10 ("IL-10"), and especially Interleukin-6 ("IL-6"). Because IL-6 is the preferred cytokine for the purposes of the present invention, it is used below to illustrate the invention's use of cytokine levels as predictors of post-trauma complications.

Serum, blood, or plasma are the preferred biological fluids for analysis of IL-6 levels. However, other biological fluids such as cerebrospinal fluid (CSF), urine, peritoneal fluid, pleural fluid, and joint fluid, etc., which contain IL-6 may alternatively be analyzed.

As used herein, the term "trauma" refers to damage to tissue that provokes an inflammatory response in an individual. Trauma results from force applied to the body, and may be either "blunt" or "penetrating," depending upon whether the immune system defense provided by the skin has been compromised. Example of "blunt" trauma include: a fall, a simple fracture, a crush (as by machinery, trampling or vehicular accident), a burn, etc. Example of "penetrating" trauma include: a wound (e.g., gun shot wound, insect or animal bite, knife wound, laceration caused by machinery, glass, etc.), a complex fracture, a surgical procedure, etc. The methods of the present invention can also be used to predict a patient's predisposition to complication where the patient has experienced any non-trauma pathological processes (such as a poisoning, a ruptured appendix, a stomach or intestinal ulcer, etc.).

The post-trauma "complication" that may be predicted using the methods of the present invention includes infection (either viral, bacterial, or protozoan), organ failure, transplant rejection, graft rejection, etc. The capacity to predict infection is of particular concern to the present invention. Infection is an unfortunate risk associated with trauma. In some instances, such infection (particularly pneumonia, intra-abdominal abscess, and/or empyema) may overwhelm the patient's immune system, and lead to death. Indeed, septicemia (the presence of pathogens or toxins in the circulatory system), and bacteremia (the presence of bacterial infection in the circulatory system) are major causes of post-trauma mortality.

The severity of a trauma can be characterized using the Injury Severity Score ("ISS") that is associated with such trauma. The ISS is a widely used method for classifying injury (Smejkal, R. et al., *Accid. Anal. Prev.* 21:386–389 (1989); Friedland, L. R. et al., *Ann. Emerg. Med.* 23:203–207 (1994); Baxt, W. G. et al., *Ann. Emerg. Med.* 19:1396–1400 (1990); Champion, H. R. et al., *J. Trauma* 29:1664–1666 (1989); Deane, S. A. et al., *Austr. N. Z. J. Surg.* 58:463–470 (1988); all herein incorporated by reference). The Abdominal Trauma Index is a classification method that is widely used to quantify the risk of complications following abdominal trauma (Borlase, B. C. et al., *J. Trauma* 30:1340–1344 (1990); Champion, H. R. et al., *J. Trauma* 29:1664–1666 (1989); Moore, E. E. et al., *J. Amer. Coll. Nutr.* 10:633–648 (1991)). These indices provide an objective means for describing and recording the extent or severity associated with a clinical condition.

As used herein, the term "predisposition" is intended to refer to the susceptibility of the patient to post-trauma complication. The invention permits a determination of such predisposition prior to the actual recognition of overt clinical symptoms (such as fever, endotoxin detection, antigen detection, etc.).

In accordance with the methods of the present invention, a patient's blood is drawn for IL-6 analaysis after the occurence of the trauma. Preferably, such blood is drawn from about 12 hours to about 36 hours post-trauma. Most preferably, such blood is drawn about one day (e.g., from about 18 hours to about 30 hours post-trauma. In the most preferred embodiment, such blood is drawn about about 24 hours post-trauma.

IL-6, secreted by lymphocytes, macrophages, and various endothelial and mesangial cells following injury accumulates in the portal vein. Thus, the IL-6 concentration in the portal vein is higher than the IL-6 level in other parts of the circulatory system. The high levels of IL-6 in the portal vein suggests that the gastrointestinal lymphoid tissue is the primary source of IL-6 secretion following injury. Unfortunately, the portal vein is relatively inaccessible. Thus, most preferably, blood used to assess IL-6 levels is drawn from the peripheral blood. The IL-6 levels of such peripheral blood correlate with a patient's predisposition to complication. If the blood is not to be processed immediately, it may be stored at low temperature (e.g., −17° C.).

Any of a variety of IL-6 assays may be used to determine the IL-6 levels in the sample. Most preferably, however, an ELISA or other immunoassay format will be employed, since such assays are generally more rapid than bioassays. Preferred assay formats are described in detail below.

The predisposition of a patient to infection is most preferably determined by evaluating the IL-6 levels in relationship to other variables, such as the extent of trauma, the age of the patient, the manner of feeding, or the Injury Severity Score and/or the Abdominal Tauma Index associated with the trauma experienced by the patient. The correlation between such predisposition and the level of a cytokine can be represented as a "predisposition equation" such as:

$$P = (a[IL-6]) + (b[MI]) + (c[ISS]) + (d[ATI]) + (e[Age]) + (f[Feeding]) - z$$

wherein P is the predisposition sum; [IL-6] is the measured concentration of IL-6 in the sample (expressed as pg/ml); [MI] is the mechanism of injury, and is either 0 (where the injury was penetrating) or 1 (where the injury was blunt); [ISS] is the Injury Severity Score and [ATI] is the Abdominal Trauma Index for the affected patient. [Age] is the patient's age specified in years. [Feeding] has a value of 0 for enteral feeding and a value of 1 for total parenteral nutrition (TPN), and wherein a, b, c, d, e, f and z are weighting factors, and wherein a has a value that ranges from greater than 0 to about 0.01; b has a value that ranges from 0 to about 3; c has a value that ranges from 0 to about 1.0; d has a value that ranges from 0 to about 0.1; e has a value that ranges from 0 to about 0.2; f has a value that ranges from 0 to about 4; and z has a value that ranges from about 2 to about 20.

A predisposition sum (P) greater than zero indicates that the patient being evaluated is predisposed to post-trauma complications. The more positive the predisposition sum, the greater that patient's predisposition to post-trauma complication.

The values of the weighting factors can be determined in a two-step process. In the first step, a decision is made as to which variables should be considered and which should be excluded. Thus, for example, if one desires a predisposition equation that does not consider the age of the patient, the weighting factor for age (e) is set to zero. Conversely, one may wish to evaluate the contribution of an additional variable (e.g., patient weight, history of smoking, history of diabetes, history of immunodeficiency disease or immunocompromising disorders, etc.) to the patient's predisposition to post-trauma complications. Thus, the first step comprises deciding which variables are to be used in the analysis.

In the second step, a group of patients is scored for each variable which has been selected for inclusion in the predisposition equation. The patients are then monitored to identify and score those who experience post-trauma complications. The desired predisposition equation is obtained by subjecting the scoring data to a multivaried analysis for the selected variables using the logistic procedure. Significance for discrete (categorical) variables can be determined with the chi-squared test of homogeneity or Fisher's exact test; all continuous variables can be tested with either the t test or the Mann-Whitney U test. Before making each t test, the assumption of equal or unequal variances with a f test is preferably determined and the appropriate t test is used. Two-way analysis of variance can be used to assess differences for infected and non-infected patients.

For example, in one suitable predisposition equation, pertaining to blunt injuries, all weighting factors except a and z are zero (and thus there is no need to evaluate the ISS and ATI associated with the trauma of the patient, or the patient's age, or the manner of feeding):

$$P = (a[IL-6]) - z$$

Preferred values for the weighting factors a and z (in a predisposition equation for a blunt injury in which all weighting factors except a and z are zero) are about 0.0081 and 2.7, respectively.

Where one wishes to exclude the mechanism of injury from the analysis, the weighting factor b is set to zero, and the predisposition of a patient to post-trauma complication can be described by the relationship:

$$P = (a[IL-6]) + (c[ISS]) + (d[ATI]) + (e[Age]) + (f[Feeding]) - z$$

wherein a is preferably about 0.004; c is preferably about 0.18; d is preferably about 0.2; e is preferably about 0.07; f is preferably about 2.8 and z is preferably about 18.

The most preferred "predisposition equation" is:

$$P = (0.0022 \times [IL-6]) + (1.82[MI]) + (0.7[ISS]) + 0.08([ATI]) - 7.6$$

The most preferred predisposition equation accurately predicted 82.5% of those patients who were infected. With a probability level of 0.5, this equation provided a sensitivity of 56.3%, a specificity of 91.5%, a false-positive rate of 30.8%, and a false-negative rate of only 14.0%. As will be appreciated, a false-positive result has little clinical significance, since it translates only into a heightened level of care to the affected patient. In contrast, the low false-negative result indicates that the method is nearly 90% effective at discerning individuals at risk of life-threatening complications.

Thus, in accordance with the present invention, standard methods are used to determine the ATI and ISS of the patient whose predisposition to complication is being evaluated. The mechanism of injury is determined based upon whether the trauma resulted from blunt force (such as a blow, or crush injury), or penetrating force (such as surgery, wounds, burns, etc.). These values are then used in the predisposition equation to determine the patient's predisposition to post-trauma complication. Such information is used to define the requisite care and therapy for the patient. Thus, patients who are found to have such a predisposition may be administered antibiotics, or may be retained under heightened observation by medical personnel. Conversely, the absence of such a predisposition may be considered in determining whether to discharge an apparently recovering patient from a hospital.

II. Methods For Determining IL-6 Concentration

IL-6 concentration can be determined using either bioassays or immunoassays or their equivalent. Because of their capacity to report results in a matter of hours rather than days, immunoassay formats or their equivalent are preferred.

Such preferred assays exploit binding molecules that have the ability to specifically bind to IL-6. As used herein, a molecule is said to be capable of "specific binding" to another molecule, if such binding is dependent upon the respective structures of the molecules. The known capacity of an antibody to bind to an immunogen is an example of "specific binding." Such interactions are in contrast to non-specific binding that involve classes of compounds, irrespective of their chemical structure (such as the binding of proteins to nitrocellulose, etc.) Most preferably, the antibody and other binding molecules of the present invention will exhibit "highly specific binding," such that they will be incapable or substantially incapable of binding to closely related molecules.

Antibodies to IL-6 are the preferred IL-6 binding molecules, however, any ligand that is capable of binding IL-6 may be employed. Such ligands include the IL-6 receptor protein, or fragments of thereof (Taga, T. et al., In: *Cellular and Molecular Mechanisms of Inflammation*, Academic Press, NY, pp. 219–243 (1990), herein incorporated by reference).

The antibodies that can be used in accordance with the present invention may be either monoclonal or polyclonal. Any of a variety of methods can be used to permit the production of polyclonal antibodies that are capable of specific binding to a IL-6 antigen. Most preferably, IL-6, or a peptide fragment of IL-6 will be used as an "immunogen" and injected into a mouse or other suitable animal.

BALB/c mice are preferred for this purpose, however, equivalent strains may also be used. The animals are preferably immunized with approximately 25 μg of the immunogen, emulsified 1:1 in TiterMax adjuvant (Vaxcel, Norcross, Ga.). Immunization is preferably conducted at two intramuscular sites, one intraperitoneal site, and one subcutaneous site at the base of the tail. An additional i.v. injection of approximately 25 μg of peptide is preferably given in normal saline three weeks later. After approximately 11 days following the second injection, the mice may be bled and the blood screened for the presence of antibodies to IL-6. Preferably, a direct binding ELISA is employed for this purpose.

Where monoclonal antibodies are desired, a mouse exhibiting the highest titer of anti-IL-6 antibody is given a third i.v. injection of approximately 25 μg of additional peptide. The splenic leukocytes from this animal may be recovered 3 days later, and are then permitted to fuse, most preferably, using polyethylene glycol, with cells of a suitable myeloma cell line. A preferred myeloma cell line is the P3X63Ag8.653 myeloma cell line. Hybridoma cells are selected by culturing the cells under "HAT" (hypoxanthine-aminopterin-thymine) selection for about one week. The resulting clones may then be screened for their capacity to produce monoclonal antibodies ("mAbs) to the IL-6 antigen, preferably by direct ELISA.

High level production of the such antibodies can be obtained using nude mice that have been primed with 0.5 ml of 2,6,10,14-tetramethypentadecane (Aldrich, Milwaukee, Wis.). After approximately 5 days, each clone is harvested, pelleted, and resuspended in sterile PBS to a final density of approximately $2.5 \times 10^6$ cell/ml. A pair of nude mice is preferably injected for each monoclonal antibody. Antibody may be recovered from the ascites fluid of the animals, and is preferably lipocleaned with Seroclear (Calbiochem, San Diego, Calif.) following vender specifications. The mAbs may then be further purified, preferably using a GammaBind Plus Sepharose column (Pharmacia, Uppsala, Sweden). Eluted MAb is preferably concentrated and dialyzed against saline. The concentration of the antibody may be determined using absorbance of light at 280 nm. Monoclonal antibodies can be isotyped using the Mouse MonoAB ID KIT (HRP) (Zymed, San Francisco, Calif.).

The above-described divalent antibody molecules (i.e. possessing the capacity to bind two molecules) comprise only one class of the immunoglobulin reagents of the present invention, however, the invention also includes derivatives and modified immunoglobulins. Thus, in one embodiment, such molecules will comprise fragments (such as (F(ab'), F(ab')$_2$) that are produced, for example, by the proteolytic cleavage of the mAbs, or single-chain immunoglobulins producible, for example, via recombinant means.

As indicated, a preferred immunoassay will employ an amount of exogenous intact IL-6 protein. In lieu of using the entire IL-6 protein, peptide fragments (such as proteolytic fragments, etc.) of the protein may be used, provided that such fragments retain a substantial capacity to bind to the IL-6 binding molecule.

The unbound reactant (e.g., exogenously added IL-6, or antibody, etc.) may be detectably labeled in order to facilitate the determination of IL-6 concentration. Enzymes are a preferred label, however, radioisotopic, paramagnetic, fluorescent, etc. labels may be employed. Such labels may be directly conjugated to or incorporated in, the reactant, but, especially in the case of enzyme labels, such labeling will preferably be accomplished by forming a biotinylated derivative of the reactant, and permitting that derivative to bind to an avidin-enzyme conjugate. Methods of biotinylation are described Kourilsky et al., (U.S. Pat. No. 4,581,333) and by Harriman, G. R. (In: *Current Protocols in Immunology*, vol. 1., Coligan, J. E. et al., eds., Greene Publishing Associates and Wiley-Interscience, New York, NY, p. 6.5.1 (1991)), both herein incorporated by reference. Horseradish peroxidase and alkaline phosphatase are preferred enzyme labels. The extent of immobilized enzyme can be readily determined using, for example, chromogenic substrates and analytical spectrophotometers.

Alternatively, the acetylcholinesterase-based IL-6 enzyme immunoassay described by Brailly, H. et al. (*Clin. Chem.* 4.0:116–123 (1994), herein incorporated by reference) may be employed.

As will be understood from the well-known principles of immunoassays, alternative formats, such as immunometric assays (also known as a "two-site" or "sandwich" assays), including both "forward," "simultaneous" and "reverse" assays may be employed. In "forward" assays, the antibody is bound to the solid phase, and then first contacted with the sample being evaluated for IL-6 under conditions that permit the formation of a binary solid phase antibody-IL-6 protein complex. After incubation and washing, the support would be placed in contact with a quantity of labeled antibody specific for IL-6 (which functions as a "reporter molecule"). After a second incubation period to permit the labeled antibody to complex with the IL-6 bound to the solid support through the unlabeled antibody, the solid support would be washed a second time to remove the unreacted labeled antibody. This type of forward sandwich assay may be a simple "yes/no" assay to determine whether IL-6 protein is present or may be made quantitative by comparing the amount of retained labeled antibody with that obtained for a standard sample containing known quantities of IL-6 protein. Such "two-site" or "sandwich" assays are described by Wide, In: *Radioimmune Assay Method*, (Kirkham et al., Ed.), E. & S. Livingstone, Edinburgh, pp 199–206 (1970), herein incorporated by reference). A "yes/no" assay may be made semi-quantitative by employing limiting amounts of, or dilutions of, the IL-6-containing sample.

In a "simultaneous" assay, a single incubation step is employed in which the bound antibody and the labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In a "reverse" assay, a solution of labeled antibody is incubated with the fluid sample followed. After such incubation, the mixture is placed in contact with a solid support to which unlabeled antigen has been previously bound. After a second incubation, the solid phase is washed in a conventional fashion to free it from the residue of the sample being tested and the solution of unreacted labeled antibody. The determination of labeled antibody associated with a solid support is then determined as in the "simultaneous" and "forward" assays.

In its most preferred embodiment, the ELISA of the present invention employs an anti-IL-6 monoclonal antibody. Most preferably, such antibodies are generated, as described above, by immunizing a heterologous mammal (such as a mouse, rat, rabbit, etc.) with an antigenic peptide, and then harvesting the splenic leukocytes of the animal, and fusing them with a suitable myeloma cell, in the manner described above.

Any of a variety of solid supports may be employed in the above assays. Suitable solid supports may be composed, for example, of materials such as glass, paper, polystyrene, polypropylene, polyethylene, dextran, nylon, amylases, natural and modified celluloses, polyacrylamides, agaroses, or magnetite. The nature of the support can be either soluble to some extent or insoluble for the purposes of the present invention. The support material may have virtually any possible structural configuration so long as the bound IL-6 is capable of binding to an anti-IL-6 antibody. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding monoclonal antibody, or will be able to ascertain the same by use of routine experimentation. Most preferably, the support will be a polystyrene microtiter plate.

The immunoassays described above are "open-endpoint assays," in which substrates and co-factors are in excess, such that the assay response will vary linearly with the amount of IL-6 in the sample. Such an assay is capable of detecting concentrations of IL-6 that range from the minimum detection level of the assay to the maximum assay saturation level of the assay. This saturation level is adjustable, and can be increased by decreasing the time of reaction. Open-endpoint assays are particularly desirable in circumstances where the potential concentration of the IL-6 is unknown.

In another embodiment, "closed-endpoint assays" may be used. Such assays may have either (or both) a user-set minimum value or a user-set maximal value. An assay that provides a minimum threshold value could be used to screen patients for those with elevated levels of plasma IL-6. In a minimum level closed endpoint assay, the assay mixture may contain an inhibitor of the enzyme (and preferably, a non-competitive or un-competitive inhibitor) at a concentration such that the activity of the enzyme will be repressed unless the amount of enzyme present (which is, of course proportional to the amount of nucleic acid present in the sample being assayed) exceeds a predefined concentration. Antibody that is capable of inhibiting the enzyme's activity may be employed as an inhibitor.

In a maximum level closed endpoint assay, the concentration of a substrate or co-factor of the reporter enzyme is such as to become limiting after the reaction has been permitted to proceeded to a desired level, or until a desired time has elapsed.

In one embodiment, the sample will be applied to multiple "zones" (i.e. applications, spottings, etc.) on a test strip, or microtiter plate wherein each zone has previously received a different set of reactants, and thus is capable of responding to a different range of IL-6 concentrations. Such an assay permits visual quantitation of IL-6 concentration, and therefore avoids any need to send a sample to a laboratory possessing spectrophotometric or colorimetric analyzers. It thus is particularly suited for physicians or nurses who are tending patients at locations that lack such apparatus. It may moreover be employed by the recovering patient to monitor his/her own IL-6 levels on an outpatient basis. Thus, the present invention provides a method for the visual determination of IL-6 concentration. If more accurate determinations are required, the colorimetric response can be ascertained using a quantitative spectrophotometer. As is well understood, the degree or extent of the reaction can be controlled by the experimentalist by merely varying time, enzyme concentration, temperature, substrate, etc. until a desired response is achieved in a desired time frame.

In one embodiment, the zones will be structured such that they posess overlapping minima, such that multiple zones "light up" (i.e. exhibit a detectable response indicative of the presence of IL-6) to indicate a particular IL-6 level. For example, a test kit may have zones that are calibrated to respond to IL-6 concentrations of 50–100 pg/ml; 75–125 pg/ml; 100–150 pg/ml, etc. An actual IL-6 concentration of 150 pg/ml would cause all zones to "light up"; a concentration of 125 would cause two zones to "light up," and would cause a third zone to partially "light up."

In a second embodiment, the zones are structured to be non overlapping, such that substantially one zone will "light up" for any particular IL-6 concentration.

In either embodiment, the zones may be calibrated using different enzymes or chromogenic substrates, such that they are capable of producing responses of different color.

III. Diagnostic Kits

The present invention includes articles of manufacture, such as "kits" that have been specially adapted to contain, in close compartmentalization, reagents that facilitate the use of the above-described methods.

Any of a variety of kits may be fashioned so as to facilitate the above-described IL-6 assays. In one embodiment, such kits may comprise a solid support (such as a polystyrene microtiter plate) that has been coated with anti-IL-6 antibody. Such kits will also include a non-immobilized, enzyme-labeled anti-IL-6 antibody. The kits will preferably contain reactants (such as buffer, chromogenic substrate, etc.) sufficient to permit the detection of any such labeled antibody. In another embodiment, such kits may comprise a test strip that contains multiple zones of antibody, or enzyme substrate, such that each zone of the strip responds to a different IL-6 concentration.

The kits may also contain reagents, wash or substrate buffers, and the like, sufficient for multiple assays including standards and/or controls, as well as instructional brochures, etc.

In one kit, the following components are provided: a microtiter plate precoated with anti-IL-6 antibody; non-immobilized, enzyme-labeled, anti-IL-6 antibody; enzyme substrate; and an amount of IL-6 sufficient to provide a positive assay control. A second kit contains vials of anti-IL-6 antibody and non-immobilized, enzyme-labeled, anti-IL-6 antibody.

Having now generally described the invention, the same will be more readily understood through reference to the following examples which are provided by way of illustration, and are not intended to be limiting of the present invention, unless specified.

EXAMPLE 1

Use of IL-6 Levels To Predict Septic Complications Following Blunt and Penetrating Trauma Both clinical and laboratory studies implicate IL-6 as a mediator of hepatocyte acute-phase protein production in the inflammatory response to injury and infection. This protein response lags behind the IL-6 levels by several days in general surgery patients. To test this observation in trauma patients, IL-6, the constitutive proteins fibronectin (FBN), prealbumin (PA), and transferrin (TFN), and the acute-phase protein, C-reactive protein (CRP) were measured sequentially in 63 severely injured trauma patients requiring laparotomy. The mean Abdominal Trauma Index (ATI) was 27.8±1.5 and mean Injury Severity Score (ISS) was 27.0 ±1.5. IL-6 levels drawn on days, 1, 4 and 7 were correlated (using Spearman, Rank and Pearson Correlation Coefficients) with serum protein levels drawn on 4, 7 and 10, respectively. IL-6 was compared between 48 non-infected patients and 15 infected patients (who developed pneumonia, intra-abdominal abscess, or empyema within 15 days of injury).

IL-6 levels on day 1 (781±825) dropped significantly by day 4 (282.9±82.5, p<0.0001) and continued to fall by day 7 (197.6±85.2, p<0.0001). IL-6 levels on day 1 and day 4 were found to be significantly higher in patients who subsequently became infected compared to patients who did not sustain subsequent infection (day 1: 1473.3±147.6 vs 414.9±73.5, p<0.0001; day 4:474.5±145.2 vs 91.4±78.3, p<0.02. Comparing infected vs non-infected patients, ISS (34.6±3.3 vs 24.5±1.5, p<0.004) and ATI (35.2±4.7 vs 25.3±1.2, p<0.04) were higher in infected patients, but there was no correlation between ISS or ATI and IL-6. The correlation between IL-6 and the serum proteins evaluated is shown in Table 1.

TABLE 1

Correlation Between IL-6 and Other Serum Proteins

| Protein | Day 1/4 | Day 4/7 | Day 7/10 |
| --- | --- | --- | --- |
| FBN | −0.36 (p < .005) | −0.54 (p < .0001) | −0.67 (p < .0001) |
| PA | −0.39 (p < .002) | −0.49 (p < .0002) | −0.54 (p < .002) |
| TFN | not significant | −0.43 (p < .001) | −0.72 (p < .0001) |
| CRP | +0.44 (p < .0004) | +0.57 (p < .0001) | +0.56 (p < .002) |

The analysis shows that an inverse relationship existed between IL-6 and the proteins FBN, PA and TFN at all periods except with respect to TFN at the ¼ sample. A positive correlation occurred between CRP and IL-6 at all points.

In sum, the data shows that significantly higher IL-6 levels on day 1 were associated with the subsequent development of infectious complications following severe trauma independent of ATI and ISS. IL-6 levels correlate positively with the acute-phase protein CRP and inversely with the constitutive proteins FBN, PA and TFN in acutely injured trauma patients and appear to influence the hepatic acute-phase protein response to injury.

EXAMPLE 2

Determination of a Quantitative Correlation Between IL-6 Levels and the Postoperative Development of Septic Complications As indicated above, IL-6 production is an integral part of the immunologic response to injury, infection, and stress. Nevertheless, efforts to use IL-6 kinetics to predict the onset of post-trauma complications have not led to a successful correlation. In order to determine the parameters and nature of a successful correlation between IL-6 levels and a patient's predisposition to post-trauma complications, the kinetics of IL-6 production was studied.

Venous blood was drawn from patients on the 1st, 4th, and 7th postoperative day in order to determine whether IL-6 levels in such blood could be used to predict subsequent infectious complications. The ability to identify those patients at risk of these complications improves the potential for identification of patients at high risk of sepsis, particularly for protocols involving therapeutic manipulation in the post-injury period, and thus reduces unnecessary entry of patients into a study.

Sixty-three patients undergoing emergency celiotomy had venous blood drawn on the 1st, 4th, and 7th day following injury. The average age of patient entering the protocol was 30.8±1.4 years with an average ISS of 27.0±1.5 and an ATI of 27.8±1.5. They received an average of 5.8±1.2 units of blood within the first 24 hours and 9.2±2.1 units of blood during the entire hospitalization. Length of stay averaged 19.6±3.3 days. Twenty patients sustained blunt trauma; 43 sustained penetrating trauma.

The 63 patients comprised the first 63 individuals who had entered into a larger study investigating the effect of route of nutrition on septic outcome. Blood was drawn on the morning following admission and on days 4 and 7 between 8 and 10 a.m. Patients entering the protocol were 18-years-of-age or greater and sustained intra-adbominal injuries with an Abdominal Trauma Index (ATI)≧15. Surgical and medical management of these patients was described in previous publications.

Serum and plasma were stored at −17° C. and subsequently analyzed for IL-6 using the methods of Aarden et al. (Aarden et al., *Eur. J. Immunol.* 17:1411–1416 (1987); Aarden et al., *Lymphokines* 10:175–185 (1985)). This bioassay detects the presence of hybridoma growth factor using the B-Cell hybridoma cell line B-9, which is dependent upon the addition of IL-6 for in vitro growth. $1 \times 10^3$ B9 hybridoma cells were seeded into 96-well flat bottom cultured plates in RPMI media containing 10% bovine serum, 5 ml 2-mercaptoethanol, 4 mmol/glutamine and 4 mg/ml gentamycin. The samples were then added to triplicate wells in two-fold dilutions and tested in parallel against a standard preparation of IL-6. Plates were cultured for 72 hours at 30° C. in 5% $CO_2$ and proliferation determined by incorporation of tritiated thymidine (1 mCi/well) during the last four hours of culture. One unit of IL-6/ml is defined as the concentration that leads to half-maximal incorporation into the assay.

Septic morbidity was defined as pneumonia, intra-abdominal abscess (IAA), or empyema occurring during the first 15 days postinjury. Pneumonia was defined as fever, leukocytosis, positive sputum/bronchoalveolar lavage specimens or purulent sputum with the development of a new pulmonary infiltrate. Response to antibiotic therapy for a cultured organism was considered confirmatory in questionable cases. Pulmonary contusion and pleural effusions were excluded as causes of the source of infiltrate after evaluation of sequential chest x-rays and a thoracentesis. Intra-abdominal abscess or empyema was defined as the presence of a purulent collection in the abdominal or thoracic cavity after drainage by laparotomy, thoracostomy tube, or computed tomography-directed catheter placement.

All infections were treated after diagnosis by the surgeons delivering the postoperative care. At the time of hospital discharge, all charts were reviewed by the principal author for confirmation of infection. The charts of those patients in whom the presence of infection was not clear were reviewed by a second surgeon blinded to therapy, and this determination was considered definitive for the presence or absence of infection.

Using these criteria, forty-seven patients remained non-infected while 16 developed either a pneumonia (12 instances), an intra-abdominal abscess (3 instances), and/or empyema (2 instances). There were no significant differences in age between non-infected and infected patients (30.7±1.8 years vs 31.3±2.1 years). Non-infected patients had significantly lower ISS and ATI values than patients who subsequently developed infections (ISS: 24.5±1.5 vs 34.6±3.3, p<0.004) and (ATI: 25.3±1.2 vs 35.2±4.7, p<0.04). Serum IL-6 levels were significantly greater in infected than in non infected patients on days 1 and 4. IL-6 levels in the infected and the non-infected group were significantly lower on days 4 and 7 than on the first blood draw. There was no correlation between the ATI/ISS in serum IL-6 levels on any day.

A multivaried analysis for the variables: IL-6, blunt and penetrating trauma, ISS, and ATI was performed using the logistic procedure. Significance for discrete (categorical) variables was determined with the chi-squared test of homogeneity or Fisher's exact test; all continuous variables were tested with either t test or Mann-Whitney U tests. Before making each t test, the assumption of equal or unequal variances with a f test was determined and the appropriate t test was used. Two-way analysis of variance was used to assess differences for infected and non-infected patients, and ISS and ATI scores. A repeated analysis of variance compared IL-6 levels over time. The likelihood of infection was found to fit the equation:

$$P = (0.0022 \times [IL\text{-}6]) + (1.82[MI]) + (0.7[ISS]) + 0.08([ATI]) - 7.6$$

where MI (mechanism of injury) is either penetrating=0 or blunt=1. If the sum of this equation was greater than 0, it was found to accurately predict (82.5%) those patients who were infected. With a probability level of 0.5, this equation provided a sensitivity of 56.3%, a specificity of 91.5%, a false-positive rate of 30.8%, and a false-negative rate of 14.0%.

Systemic IL-6 levels were found to correlate with the acute-phase protein response by the liver and positively correlate with the depression in the constitutive protein production of transferrin, prealbumin, and fibronectin and positively with the secretion of C-reactive protein. The experiment thus demonstrates that the initial secretion of IL-6 by the body predicts patients who subsequently develops the septic complications of pneumonia, intra-abdominal abscess, and/or empyema confirming the work of Baigrie, R. J. et al. (Amer J. Surg. 166:248–251 (1993)) who correlated subsequent complications with serum IL-6 levels following abdominal surgery. It is particularly interesting that the ATI and ISS which have been used to predict subsequent septic complications although somewhat imprecisely, failed to correlate with serum IL-6 levels and demonstrate that current, common scoring mechanisms used to assess the degree of trauma do not predict cytokine response of IL-6 by the gastrointestinal tract to injury. The exact trigger for the levels of serum IL-6 are unknown but appear to be related to the secretion of TNF and interleukin-1 secretion by the body. Whether hypoperfusion of the gastrointestinal tract, the magnitude of cellular damage induced by trauma or some other factor generates a serum IL-6 response in proportion to this trigger is unknown, but early IL-6 levels were measured by cytoproliferative assays can be used to predict the subsequent development of septic complications. This is useful for the recruitment of patients into protocols assessing the effectiveness of biotechnological, antibiotic, or other regimens to improve patient outcome by minimizing the number of patients entered into protocol who subsequently do not develop infection and by identifying a higher percentage of patients likely to get infection. As a result of this identification, fewer patients could be entered into protocol and the effectiveness of therapeutic regimens determined using populations of smaller size. At present, it is unclear whether ELISA techniques for determining IL-6 in a rapid basis will provide the same results as cytoproliferative assays, and preliminary work would suggest that it does not. This is perhaps because cytoproliferative assays measure other factors circulating in the serum which can effect cellular response while ELISA techniques measure IL-6 alone.

While portal samples of IL-6 might permit even better predictions of which patients are at risk of developing septic complications, access to the portal system 24 hours following injury is difficult. Moore, E. E. et al. (J. Amer. Coll. Nutr. 10:633–648 (1991)) were able to chronically correlate the portal vein in trauma patients in a study which demonstrated no window toxemia or bacteremia in the first five days. However, these investigators did not measure portal vein levels of various cytokines in this response.

Serum IL-6 levels correlate with the subsequent development of major infectious complications. While these serum levels may reflect hypoperfusion of the gastrointestinal tract with a subsequent immunologic response or a "sensing" of the gut immunologic system to peripheral trauma, serum levels may be used to predict patients at risk of developing septic complications and other major postoperative complications.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for determining the predisposition of an individual subjected to a blunt trauma to a complication of said trauma prior to the onset of overt clinical symptoms of such complication, which comprises determining the concentration of the cytokine, Interleukin-6 present in a biological fluid of said individual about one day post-trauma, wherein said method comprises the steps:

(A) determining the concentration of Interleukin-6 in the biological fluid of said individual subjected to said trauma; and (B) correlating said determined serum concentration with the mechanism of injury (MI) of said trauma, the Injury Severity Score (ISS) of the severity of said trauma, or the Abdominal Trauma Index (ATI) of said trauma to thereby determine said individual's predisposition to complication of said trauma prior to the onset of overt clinical symptoms thereof.

2. The method of claim 1, wherein said blunt trauma is a poisoning, a fall, a simple fracture, a crush or a burn.

3. The method of claim 1, wherein said complication comprises an infection.

4. The method of claim 3, wherein said infection is septicemia or bacteremia.

5. The method of claim 3, wherein said infection is pneumonia.

6. The method of claim 3, wherein said infection is an intra-abdominal abscess.

7. The method of claim 3, wherein said infection is empyema.

8. The method of claim 1, wherein said determination of said cytokine concentration is accomplished by an immunoassay.

9. The method of claim 8, wherein said immunoassay is an enzyme linked immunosorbent assay.

10. The method of claim 8, wherein said immunoassay is an open-endpoint immunoassay.

11. The method of claim 8, wherein said immunoassay is a closed endpoint immunoassay.

12. The method of claim 8, wherein said immunoassay employs a monoclonal antibody, said monoclonal antibody binds to said cytokine.

13. The method of claim 8, wherein said immunoassay employs a polyclonal antibody, said polyclonal antibody binds to said cytokine.

14. The method of claim 1, wherein said biological fluid is selected from the group consisting of blood, plasma or serum.

15. The method of claim 1, wherein said biological fluid is selected from the group consisting of cerebrospinal fluid (CSF), peritoneal fluid, pleural fluid, and joint fluid.

16. The method of claim 1, wherein said biological fluid is urine.

* * * * *